United States Patent [19]

Scharnberg et al.

[11] Patent Number: 4,779,630
[45] Date of Patent: Oct. 25, 1988

[54] DEFIBRILLATOR PAD ASSEMBLY AND METHOD FOR USING SAME

[75] Inventors: Lorne C. Scharnberg; Ronald G. Eklund, both of Des Moines, Iowa; Warren R. Walters, Lakeville, Minn.

[73] Assignee: Katecho, Inc., Des Moines, Iowa

[21] Appl. No.: 98,487

[22] Filed: Sep. 18, 1987

[51] Int. Cl.$^4$ .............................................. A61N 1/00
[52] U.S. Cl. .................................. 128/783; 128/798; 128/800
[58] Field of Search ............... 128/783, 798, 800, 802, 128/803, 640, 303.13, 303.14, 303.17, 303.18, 82.1, 362, 390, 379

[56] References Cited

U.S. PATENT DOCUMENTS

| | | | |
|---|---|---|---|
| 3,685,645 | 8/1972 | Kawaguchi | 128/803 |
| 3,702,613 | 11/1972 | Panico et al. | 128/803 |
| 3,961,623 | 6/1976 | Milani et al. | 128/803 |
| 4,387,714 | 6/1983 | Geddes et al. | 128/303.13 |
| 4,524,087 | 6/1985 | Engel | 128/802 |
| 4,633,879 | 1/1987 | Ong | 128/798 |

*Primary Examiner*—Francis J. Jaworski
*Assistant Examiner*—George Manuel
*Attorney, Agent, or Firm*—Zarley, McKee, Thomte, Voorhees & Sease

[57] ABSTRACT

The pad assembly of the present invention is adapted to be used with a defibrillator paddle. The assembly includes a bottom sheet and a top sheet, with a flexible second sheet sandwiched therebetweeen. The second sheet is comprised of an electrically conductive polymer having the characteristic of being inherently adhesive on both of its upper and lower surfaces. The upper and lower surfaces are detachably adhered to the top and bottom sheet members. A tab is operatively attached to the second sheet member so as to permit manual grasping of the second sheet member without engaging the adhesive upper and lower surfaces of the second sheet member. The device is used by removing the bottom sheet member from the second sheet member, and by placing the second sheet member in covering relation over the electrodes of a defibrillator paddle. When the defibrillator is used on a patient, and top sheet member is removed and the tacky second sheet member is placed in contact with the patient's chest.

14 Claims, 2 Drawing Sheets

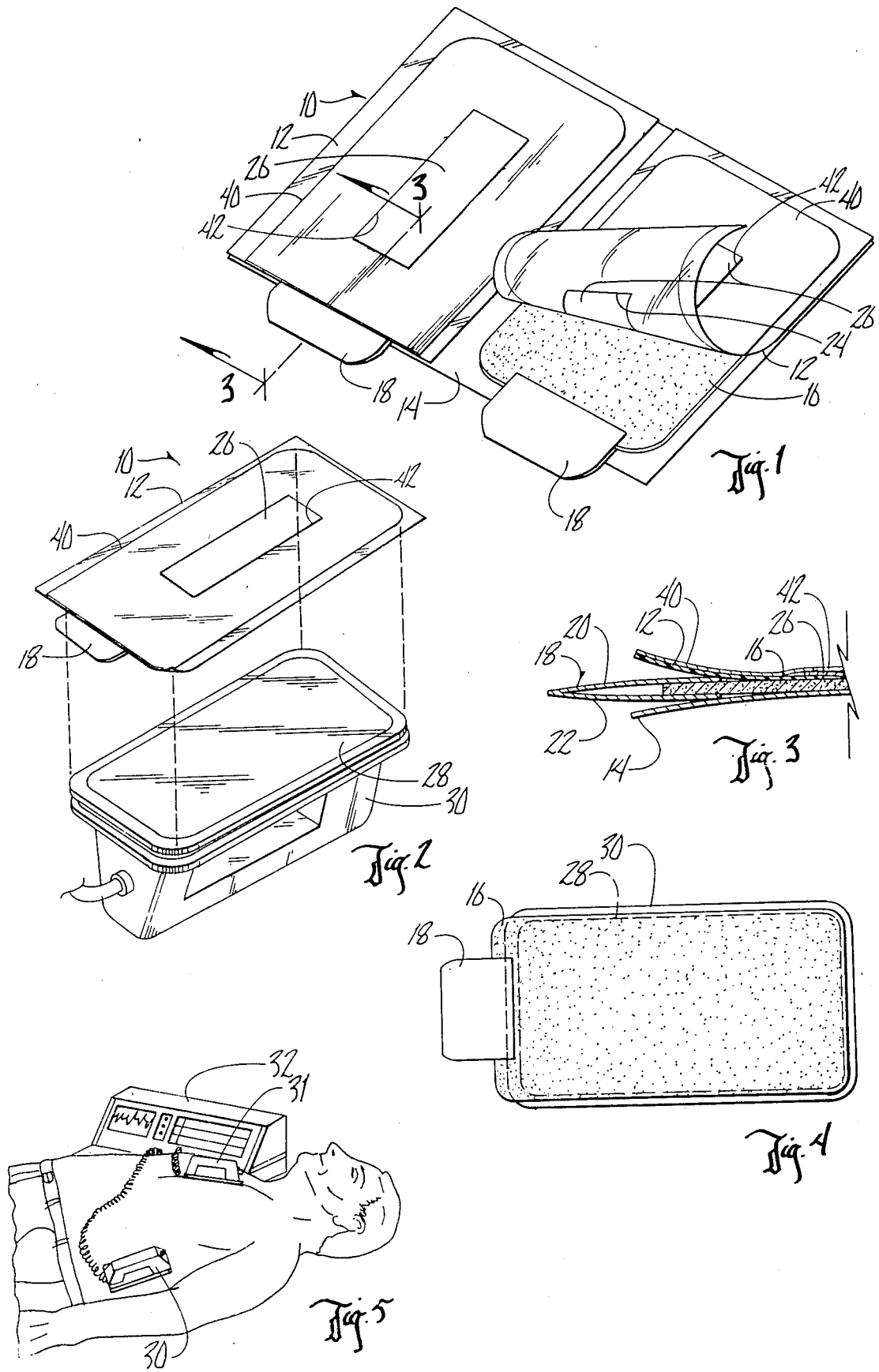

DEFIBRILLATOR PAD ASSEMBLY AND METHOD FOR USING SAME

BACKGROUND OF THE INVENTION

The present invention relates to a defibrillator pad assembly and a method for using same.

Defibrillation is a process used for patients encountering fibrillation of the heart. The defibrillation process involves placing two electrode paddles on the patient's chest and applying a high density electrical current to the patient so as to stimulate the heart and correct the fibrillation of the heart.

Dry skin on a patient causes the interface between the metal defibrillator paddles and the skin to have a high impedance. This can cause severe skin burns and may cause a significant enough reduction in the current delivered to the heart to prevent successful defibrillation.

Present methods for applying the defibrillator paddles to the skin involve the use of electrically conductive gels which are applied to the patient's skin and which are also applied to the defibrillator paddles. Often the gel is incompletely applied, leaving bare spots between the paddle and the patient's skin. These bare spots may result in burning of the patient's skin during discharge. Also, it is necessary for the user of the paddles to continue to apply pressure between the paddle and the patient's skin so as to insure a positive electrical contact therebetween. The gels do not provide adhesive strength to hold the paddles in place without the operator holding the paddles. Another disadvantage of presently used gels is that the gels can run down the cord of the defibrillator and shock the user during use. The user cannot remove his hands from the defibrillator paddles because the paddles will slide or move away from the proper positioning. It is therefore necessary for the operator to keep both hands on the paddles during the use of the present conductive gels.

Another presently used method for defibrillating involves the use of moisturized polymer pads which are enclosed within an airtight envelope. The pads are removed from the envelope and placed on the patient's chest immediately prior to use. Then the defibrillator paddles are placed over the pads in preparation for their use. The disadvantage of these moisturized pads is that they tend to harden and become brittle after prolonged exposure to the atmosphere. Another disadvantage is that the package holding the pads has to be opened at the time of the emergency to get access to the pads. They can only be used once, and then must be discarded. Furthermore, they do not provide a strong adhesive bond between the patient's chest and the paddles, and therefore as is the case with the use of gels, the operator must continue to keep both hands on the paddles in order to hold them in place.

None of the present methods for defibrillating permit the defibrillator paddles to be pre-loaded with conductive pads prior to the time the patient is encountered. The moisturized pads cannot be removed from their sealed envelopes until just prior to their application to the patient's chest. They cannot be pre-applied to the paddles and stored with the paddles in the defibrillator machine.

Therefore, a primary object of the present invention is the provision of an improved defibrillator pad assembly and method for using same.

Another further object of the present invention is the provision of a defibrillator pad assembly which utilizes conductive pads which can be placed on the defibrillator paddles and used a number of times on the same patient.

A further object of the present invention is the provision of an improved defibrillator pad assembly which utilizes a pad which can be placed on the defibrillator paddles and stored with the paddles in the defibrillator machine well in advance of the time that the paddles are used for a patient.

A further object of the present invention is the provision of an improved defibrillator pad assembly which utilizes conductive pads which are placed on the defibrillator paddles, and which are stored on the defibrillator console with the paddles.

A further object of the present invention is the provision of a conductive defibrillator pad assembly which can be stored with a defibrillator console, and which permits repeated testing of the defibrillator pad assembly prior to use.

A further object of the present invention is the provision of an improved defibrillator pad assembly which utilizes a conductive polymer sheet having an inherently adhesive upper and lower surface, and which is water or alcohol soluble.

A further object of the present invention is the provision of an improved defibrillator pad assembly which utilizes a polymer which is not moist, and which does not dry, which does not lose its adhesive characteristic, and which does not become brittle after prolonged exposure to the atmosphere.

A further object of the present invention is the provision of an improved defibrillator pad assembly which provides an adhesive conductive polymer which holds the paddles to the patient's chest, and which permits the operator to remove his hands from the paddles while administering to the patient.

A further object of the present invention is the provision of an improved defibrillator pad assembly which is not toxic to the human skin.

A further object of the present invention is the provision of an improved defibrillator pad assembly and method for using same which is economical, efficient in operation, and inexpensive.

SUMMARY OF THE INVENTION

The present invention provides good electrical conduction between the dry skin of the patient and the dry metallic surface of the defibrillator paddles. This insures effective defibrillation and monitoring, and also minimizes the hazard of severe burns to the patient.

The conductive pad used with the present invention can be pre-applied to the defibrillator paddles and stored with the paddles in the defibrillator machine prior to encountering a patient. When a patient is encountered, the user can quickly remove the paddles from the machine, strip off a protective sheet member from each conductive pad, and place the paddles having the pads thereon in engagement with the patient's chest. This is a much quicker process than the prior method of removing the pads from an envelope, placing them on the patient's chest, and then placing the paddles over the pads. It is also advantageous over prior methods because the operator can remove his hands from the paddles and the paddles and pads will adhere to the patient's chest and remain in place. This frees the operator's hands for other tasks.

The conductive pad used with the present invention is a conductive polymer purchased from Promeon Division of Medtronic, Inc., 6951 Central Avenue N.E., Minneapolis, Minn. 55440, under the product designation RG 63 A, or RG 63 B. The conductive polymer includes thin fibers of polyethylene scrim which run through the polymer and which give the polymer sheet strength. The scrim may also be made of other materials, such as carbon, nickle coated carbon or other materials. The conductive pad is shaped to fit the metal electrodes of the paddles. It has a strong tacky characteristic which causes it to adhere both to the patient's skin and to the metal surface of the paddle electrodes. It does not dry out as previous pads, and retains its tackiness throughout prolonged exposure to the atmosphere. Furthermore, the conductive pad of the present invention adheres to the metal of the paddle electrodes with a stronger force than it adheres to the patient's skin, and accordingly, it can be removed from the patient merely by lifting up on the electrode paddles.

The conductive polymer sheet of the present invention also includes on its upper surface a protective sheet member and on its lower surface a protective sheet member. A paper tab is attached to one of the margins of the conductive polymer sheet so as to permit the polymer sheet to be grasped without encountering the tacky surface of the polymer itself.

The upper sheet member which is detachably secured over the polymer pad includes a window therein, and the window is covered by a conductive strip. The conductive strip is preferably stainless steel and is pretreated with a non-flammable, non-toxic, conductive adhesive gel. The preferred gel for this purpose is manufactured by Parker Laboratories, Inc., Orange, N.J. 07050, under the trademark "Tensive".

In using the device, the bottom protective sheet member is removed from the polymer pad, and the polymer pad is placed in contact with the metal electrode of the defibrillator paddle. The upper sheet member is left on the upper surface of the conductive polymer so as to prevent the polymer from adhering to other surfaces while it is stored on the paddle. The paddle is then placed in a receptacle on the defibrillator console with the conductive strip of the upper protective sheet member in engagement with a test electrode on the console. Thus, electrical continuity is provided between the test electrode on the console through the conductive strip and the conductive polymer to the metal electrode on the defibrillator paddle. By actuating an appropriate control on the console, it is possible to test the machine to make certain that it is properly discharging.

When the device is used for a patient experiencing fibrillation, the two paddles are removed from the receptacles on the defibrillator console. The protective sheet members are removed from the polymer so as to expose the tacky surface of the polymer. The defibrillator paddles are then placed on the patient's chest at the appropriate locations with the tacky surface of the conductive polymer in contact with the patient's skin. The polymer adheres to the patient's skin and provides a solid connection between the electrode plates of the paddle and the patient's skin. The device adheres with such strength that it is possible for the operator to remove his hands from the paddle and the paddle will remain in place. This is a significant advantage since the operator often finds it necessary to have his hands free to perform other functions while treating the patient.

Both before and after the defibrillator process, the operator can leave the paddles on the patient's chest, and the console of the defibrillator can be used to monitor the patient. Later it is possible to remove the paddles from the patient, with the conductive polymers remaining adhered to the metal surfaces of the paddle electrodes. The protective sheet member is then placed over the polymer on the paddles, and the paddles are reinserted into the console receptaclss for possible later use on the patient.

Because the conductive polymer does not dry out, become brittle or lose its adhesive characteristics, it is possible to reuse the defibrillator paddles numerous times on the same patient without the necessity of changing the conductive polymers.

BRIEF DESCRIPTION OF THE FIGURES OF THE DRAWINGS

FIG. 1 is a perspective view of the pad assemblies used in the present invention.

FIG. 2 is an exploded perspective view showing the use of the pad assembly in connection with a defibrillator paddle.

FIG. 3 is a sectional view taken along line 3—3 of FIG. 1.

FIG. 4 is a plan view of the conductive polymer in place on the metal electrode of the defibrillator paddle.

FIG. 5 is a perspective view showing the use of the defibrillator paddles on a patient.

DETAILED DESCRIPTION OF THE PREFERRED EMBODIMENT

Figure 6:
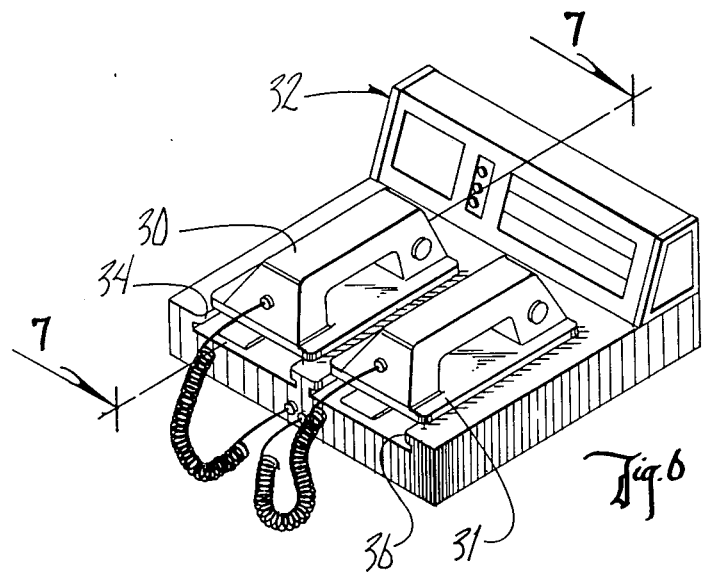
FIG. 6 is a perspective view of a defibrillator console having the defibrillator paddles stored therein.

Referring to FIG. 1, the numeral 10 refers to the defibrillator pad assembly of the present invention which comprises a pair of transparent upper release liners 12, a lower release liner 14, and a conductive pad 16. Pad 16 includes a paper tab 18 attached to the margins thereof for permitting a person to manually grasp pad 16 without encountering the tacky surface of the pad 16 itself.

Pad 16 is made of a conductive polymer manufactured by Promeon Division of Medtronics, Inc., 6951 Central Avenue N.E., Minneapolis, Minn. 55440, under the product designations RG 63 A or RG 63 B. The polymer has a scrim of polyethylene fibers which run throughout pad 16 for imparting structural integrity to the pad 16. The pad 16 is approximately 0.030 to 0.035 inches thick. The polymer from which pad 16 is made has the characteristic of being extremely tacky so that it will adhere to any surface it contacts. The adhesive polymer is water or alcohol soluble, and therefore can be removed from any surface by applying water or alcohol. The polymer is electrically conductive, and, while being extremely tacky, is not moist. It does not dry out or lose its adhesive characteristic or become brittle when exposed for prolonged periods of time to the atmosphere. It also is not toxic to the skin. When the pad 16 is exposed to both the metal of a defibrillator paddle and to the skin of a patient, the pad 16 has a stronger adhesive bond with the metal of the defibrillator paddle than with the patient's skin.

Tab 18 is constructed of a strong paper or other suitable material, and is folded over upon itself to create upper and lower flaps 20, 22, respectively. These flaps engage the upper and lower surfaces of pad 16 as can be seen in FIG. 3, and because of the adhesive characteristics of pad 16 the tab 18 is securely attached to pad 16.

The lower release liner 14 may be constructed of paper, plastic or other suitable material. It is preferably coated with a silicone release coating, so that it will adhere to pad 16 upon contact, but it can be easily removed from pad 16. Silicone release coating permits the pad 16 to be removed from release liner 14 merely by grasping tab 18 and peeling the pad 16 out of contact with release liner 14.

The upper release liner 12 is comprised of plastic or other suitable material, and includes a window 24 cut therein. Window 24 also can be a round window or any other shape. Assembly 10 can be provided in many sizes and shapes to accommodate all the various shaped paddles of the defibrillator manufacturers. This will also cause the size and shape of the window to vary. Operatively secured over the upper surface of upper liner 12 and in covering relation over window 24 is a conductive strip 26. The conductive strip 26 is in electrical contact with the upper surface of pad 16, so as to provide electrical contact to pad 16 from the upper surface of liner 12. A label 40 having a window 42 is adhered over conductive strip 26 so as to positively attach conductive strip 26 to the upper surface of upper liner 12.

The surface of conductive strip 26 engaging the upper surface of pad 16 is precoated with a thin film of nonflammable conductive adhesive gel (not shown in drawings), which insures that positive adherence and electrical contact is maintained between the conductive strip 26 and the upper surface of pad 16. The preferred gel for this purpose is manufactured by Parker Laboratories, Inc., Orange, N.J. 07050, under the trademark "Tensive". It has a honey-like consistency.

This adhesive gel also facilitates manual removal of the conductive strip from the conductive polymer after defibrillation currents are discharged through the paddles and pads. Without the use of the gel, the conductive strip may stick to the conductive polymer so strongly that it cannot be removed from the conductive polymer. The adhesive gel, while providing positive adherence, does permit the conductive strip to be manually peeled away from the conductive pad.

When the pad assembly 10 is used, the tab 18 is grasped and pad 16 is peeled upwardly off of lower release liner 14. Upper liner 12 remains attached to the upper surface of pad 16. In this condition, the pad 16 with the upper liner 12 attached thereto is placed in contact with the metal electrode plate 28 of a defibrillator paddle 30 as shown in FIG. 2. The tacky undersurface of pad 16 engages the metal plate 28, and forms a strong adhesive bond therebetween. The upper liner 12, which is preferably a transparent plastic material, remains in place over the upper surface of pad 16. FIG. 6 illustrates a typical defibrillator console 32 having a pair of rectangular receptacles 34, 36 for receiving two defibrillator paddles 30, 31, each of which is identical in construction.

Figure 7:
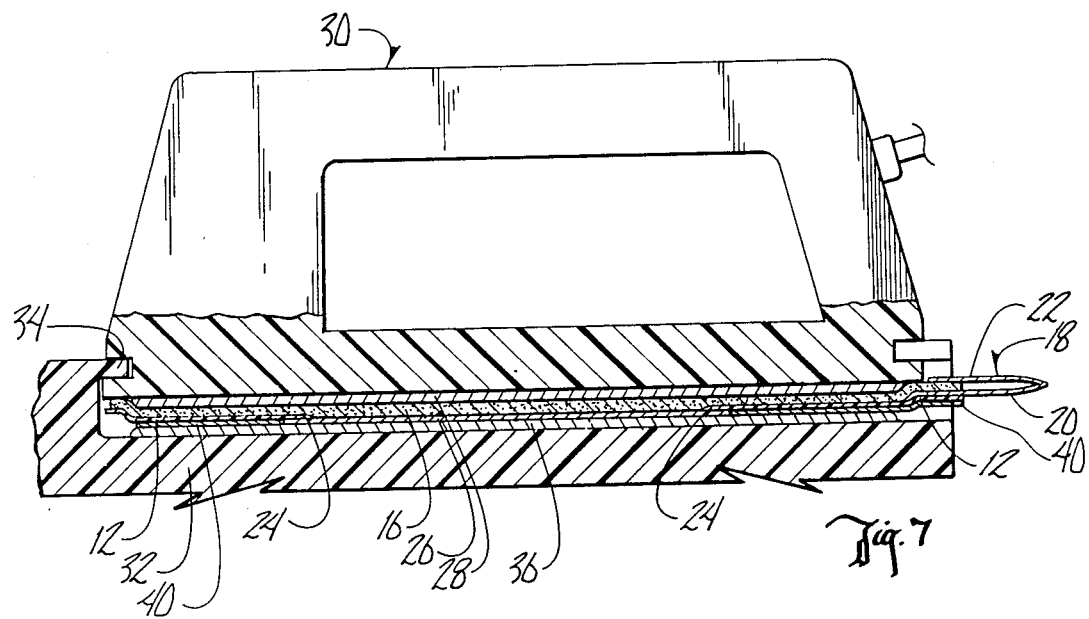
FIG. 7 is a sectional view taken along line 7—7 of FIG. 6.

As can be seen in FIG. 7, defibrillator paddle 30 includes a defibrillator electrode 28 on the lower surface thereof and adhered over this electrode 28 is the conductive polymer pad 16. It should be noted that pad 16 is slightly larger than the electrode 28 so as to completely cover the electrode 28. The protective liner 12 remains in covering relation over pad 16, and the rectangular or round piece of conductive strip 26 is placed in electrical contact with a console electrode 36 at the bottom of receptacle 34. As can be seen in FIG. 7, the conductive strip 26 provides electrical continuity from console electrode 36 to paddle electrode 28 through the conductive strip 26 and the conductive polymer 16. This permits the defibrillator paddles to be tested by manipulating the controls of console 32. Thus, the paddles 30 can be tested while in place without the need for removing protective liner 12.

When it is necessary to use the paddles on a patient, the paddles are removed from receptacles 34, 36, and the protective liners 12 are grasped and pulled away from the conductive pad 16, thereby leaving the surface of pad 16 exposed for engagement with a patient's chest. FIG. 4 illustrates a bottom plan view of the paddle 30 having conductive pad 16 thereon with the liner 12 removed.

After removal of the protective liner 12, the defibrillator pads are placed on the patient's chest similar to the manner shown in FIG. 5, with the exposed tacky surface of pad 16 in contact with the patient's chest. The tackiness of the pad 16 causes the pad to adhere to the skin of the patient, and to hold the paddles 30, 31 in place without the necessity of the operator manually holding the paddles in place. The operator's hands are free for manipulating other instruments or for doing other tasks necessary to proper administration of the patient's needs. It is possible to leave the pads 30, 31 in place, and most defibrillator consoles 32 are capable of monitoring the patient's heart during this time period. This enables the paramedic to administer to the patient while at the same time monitoring the patient's heart to make certain that defibrillation does not occur. The instant that fibrillation is sensed by the console 32, it is possible for the paramedic to administer the appropriate pulse of electricity for defibrillating the patient.

After the device has been used, the paddles 30, 31 are lifted upwardly, and the pad 16 adheres to the paddles 30, 31 with a greater strength than it adheres to the patient's skin. Thus, the pad 16 remains attached to the paddles 30, 31 after they are removed from the patient's skin. The liners 12 can again be placed over the pad 16, and the pad 16 can be reinserted into the receptacles 34, 36 of the console 32 for further use on the same patient.

The pads do not harden or lose their tackiness throughout prolonged exposure to the atmosphere, and therefore it is possible to use the pads several times on the same patient before discarding them. Furthermore, it is possible to attach the pads to the paddles prior to the time that the patient is encountered, so that the paddles will be easy to use quickly when the paramedic reaches the patient. All that is necessary is to remove the protective liner 12 and place the paddles in contact with the patient. This is substantially faster than prior methods which require the administration of jelly, or the administration of a conductive polymer to the patient's skin after opening and removing the polymer from a package. These methods require careful attention to be given to the contact between the electrodes of the paddles and the patient's skin. Any failure to achieve proper electrical contact in prior devices can result in severe burns to the patient's skin.

Thus, it can be seen that the device accomplishes at least all of its stated objectives.

What is claimed is:

1. A method for preparing a defibrillator paddle for use on a patients chest having an exposed skin surface, said method comprising:

placing a flexible electrically conductive sheet member between an upper sheet member and a lower sheet member so that said upper and lower sheet members completely cover said electrically conductive sheet member, said electrically conductive sheet member comprising an electrically conductive polymer having the charactreristic of being tacky so as to detachably adhere to most surfaces it contacts;

removing said upper sheet member from said electrically conductive sheet member so as to expose an upper face of said conductive sheet member, placing substantially all of said upper surface of said conductive sheet member in direct electrical contact with and in covering relation over the elctrode plate of said paddle whereby said conductive sheet member will form an adhesive attachment to and an electrical contact with said electrode plate;

removing said lower sheet member from said conductive sheet member so as to expose a bottom face of said conductive sheet member;

placing said paddle on said exposed skin surface of patient's chest with said exposed bottom face of said conductive sheet in direct contact with said patient's chest whereby said bottom face of said conductive sheet will detachably adhere to said skin of said patient and said conductive sheet member will form an electrical connection between said electrode plate of said pad and said patient's skin.

2. A method according to claim 1 and further comprising removing said paddle and conductive sheet member from said patient's chest and replacing said bottom sheet member in covering relation over said bottom face of said conductive sheet member while said upper surface of said conductive sheet member remains adhered to said electrode plate of said paddle.

3. A method according to claim 1 comprising placing a test electrode in electrical contact with a conductive strip on said lower sheet member before said lower sheet member is removed from said bottom face of said conductive sheet member, said conductive strip being in electrical contact with said conductive sheet member so that electrical continuity is provided from said electrode plate through said conductive sheet member and said conductive strip to said test electrode.

4. A combination comprising:
a defibrillator paddle having a rigid flat electrically conductive electrode plate;
a flexible conductive sheet member having an upper surface, a lower surface, and a perimetric edge and being comprised of an electrically conductive polymer which is flexible and inherently tacky and which retains said flexibility and tackiness when exposed to the atmosphere;
substantially all of said upper surface of said conductive sheet member being in close direct electrical contact with and substantially completely covering said electrode plate of said paddle, said inherent tackiness of said conductive sheet member causing substantially all of said upper surface of said conductive sheet member to be adhered to said electrode plate;
a dielectric cover sheet member having an upper surface, a lower surface, and a perimetric edge, said upper surface of said cover sheet member being in close contact with and completely covering said lower surface of said conductive sheet member, said inherent tackiness of said conductive sheet member causing said upper surface of said cover sheet member to be adhered to said lower surface of said conductive sheet members;
tab means attached to said conductive sheet member and having a grasping portion protruding outwardly beyond said perimetric edges of said conductive sheet member and said cover sheet member.

5. A pad assembly according to claim 4 wherein a scrim of reinforcing fibers is embedded within said second sheet member to provide structural integrity thereto.

6. A pad assembly according to claim 4 wherein said conductive polymer is soluble in water and in alcohol.

7. A pad assembly according to claim 4 wherein said conductive polymer is non-toxic to human skin.

8. A combination according to claim 4 wherein said dielectric sheet member includes a window opening extending through the thickness thereof, an electrically conductive strip attached to said upper surface of said cover sheet member in covering relation over said window opening, said conductive strip having an upper surface in electrical contact with said lower surface of said conductive sheet member and having a lower surface facing said window opening, a second electrode, said cover sheet member being positioned between said second electrode and said conductive strip, said conductive strip and said second electrode being in electrical contact with one another through said window opening so as to provide electrical continuity from said second electrode through said conductive strip and said conductive sheet member to said electrode plate of said defibrillator paddle.

9. A pad assembly according to claim 8 wherein said upper surface of said conductive strip includes a coating of conductive adhesive gel between said upper surface of said conductive strip and said conductive sheet member.

10. A combination according to claim 8 wherein said conductive strip is comprised of metal foil.

11. A combination according to claim 8 comprising a defibrillator console having a receptacle, said second electrode being attached to and contained within said receptacle and said paddle, said conductive sheet member and said cover sheet member also being removably positioned within said receptacle.

12. A combination according to claim 4 wherein a release coating is provided on said upper surface of said cover sheet member.

13. A combination according to claim 12 wherein said release coating is comprised of a silicone material.

14. A combination for use on a patient's chest having a skin surface comprising:
a defibrillator paddle having a rigid flat electrically conductive electrode plate;
a flexible conductive sheet member having an upper surface, a lower surface, and a perimetric edge and being comprised of an electrically conductive polymer which is flexible and inherently tacky and which retains said flexibility and tackiness when exposed to the atmosphere;
substantially all of said upper surface of said conductive sheet member being in close direct electrical contact with and substantially completely covering said electrode plate of said paddle, said inherent tackiness of said conductive sheet member causing substantially all of said upper surface of said conductive sheet member to be adhered to said electrode plate;

said lower surface of said conductive sheet being capable of direct electrical contact with said skin surface of said patient's chest, said tackiness of said lower surface of said conductive sheet being capable of causing said conductive sheet to adhere to said skin surface of said patient's chest with sufficient strength to detachably secure said defibrillator paddle to said patient's chest and to maintain said electrode of said paddle in electrical connection with said skin surface of said patient's chest through said conductive sheet member when said conductive strip is the ony means of securing said paddle to said patient's chest;

said conductive sheet member being the only member between said paddle electrode and said patient's skin. whenever said conductive sheet member is applied to said patient's skin.

* * * * *